United States Patent [19]

Strong

[11] Patent Number: 5,345,826

[45] Date of Patent: Sep. 13, 1994

[54] STATIC LOAD TESTER WITH I-BEAM SUPPORT COLUMN

[76] Inventor: David J. Strong, METL, Inc., 3701 W. Thomas Rd., Pheonix, Ariz. 85019

[21] Appl. No.: 57,683

[22] Filed: May 4, 1993

[51] Int. Cl.⁵ .............................................. G01N 3/08
[52] U.S. Cl. ...................................... 73/826; 73/827; 73/1 B; 73/828
[58] Field of Search ................... 73/819, 826, 827, 828

[56] References Cited

U.S. PATENT DOCUMENTS

| | | | |
|---|---|---|---|
| 1,888,755 | 10/1931 | Barr et al. | 73/826 |
| 4,292,835 | 10/1981 | Bickford | 73/1 B |
| 4,478,086 | 10/1984 | Gram | 73/826 |

FOREIGN PATENT DOCUMENTS 989369  1/1983  U.S.S.R. .................. 73/826

*Primary Examiner*—Robert Raevis
*Assistant Examiner*—James M. Olsen
*Attorney, Agent, or Firm*—James F. Duffy; Richard E. Oney

[57] ABSTRACT

A static load tester is shown that provides tensile testing of plated test specimens to detect hydrogen embrittlement damage from plating processes. The functional components of the device are centrally aligned within a channel of an I-beam frame. A load cell and electronic readout provide the user with a measure of the tensile force applied to up to eight test specimens mounted end to end in a tester. Tension is applied to the specimens through use of a simple threaded rod and nut load application system at the base of the device. A static load tester may be incorporated into each channel of the I-beam frame, thereby providing a double testing unit. Additionally, a series of I-beam frame tester configurations may be incorporated into one multiple testing unit. Each multiple testing unit has a number of static load testers equal to double the number of I-beam frames mounted into the unit. The tension applied to any individual tester in a multiple testing unit may be displayed on a single electronic readout through use of a switch box coupled between the individual testers and the readout.

11 Claims, 3 Drawing Sheets

STATIC LOAD TESTER WITH I-BEAM SUPPORT COLUMN

BACKGROUND

1. Technical Field of the Invention

This invention relates to the field of devices used for materials testing, and specifically for testing plated test specimens by applying static tension loads to the specimens for extended periods of time. The purpose of such testing is to detect hydrogen embrittlement damage incurred during plating processes.

2. Prior Background Art

The prior art is comprised of devices generally designed for stress or creep rupture testing. See FIG. 1 which shows a typical prior art device, traditionally referred to as a lever arm tester. The device consists of a lever arm of from twelve to twenty inches in length, pivotally supported on a fixed vertical member at a point along the lever arm's length between its center and an end to which the top of a test specimen is attached. The bottom end of the test specimen is attached to a fixed base plate. When weights are applied to the opposite end of the lever arm, tensile force is exerted on the test specimen as dictated by the formula $t=(wl)/d$, where t is the tensile force exerted on the test specimen, w is the weight applied to the far end of the lever arm, l is the distance between the lever arm pivot point and the end carrying the applied weights, and d is the distance between the lever arm pivot point and the end connected to the test specimen. The applied force, t, causes testing of the specimen to take place.

Prior art devices are inferior in several respects to the present invention. The twelve to twenty inches long lever arm, size, and shape of these devices require considerable floor space be reserved in testing laboratories which often have limited available floor space. Prior art testers are completely manual in operation, and must be operated by a technician skilled in the testing procedure because of their many variables and potential inaccuracies. The devices are capable of testing only one specimen, or one group of specimens, at a time, and are typically very costly.

Thus, there exists a need for a static load testing device that overcomes the problems and limitations of the prior art. The present invention is compact, easy to use, and relatively inexpensive. It requires considerably less floor space than conventional devices, and has the capacity to test multiple specimens simultaneously. This device is substantially more accurate than prior art devices, and is equipped with electronic load readouts and timers for increased efficiency and decreased reliance on manual adjustments and readings; as such, it can be operated by semi-skilled personnel. Additionally, a simple screw mechanism is used to apply tensile force to test specimens, eliminating the need for cumbersome weights.

SUMMARY DESCRIPTION OF THE INVENTION

The invention is a static load tester, to replace prior art, lever arm testers, for applying a tensile load to selected specimens over an extended period of time. The load tester comprises an I-beam support column having first and second channels. A load sensing device for outputting a signal representative of a tensile load applied to the device is disposed within the first channel of the I-beam. The load sensor has a first end coupled to the I-beam and a second end.

A tensioning apparatus is coupled to the I-beam, within the first channel, and disposed opposite the load sensing device. Means for coupling a selected test specimen between the second end of the load sensing device and the tensioning apparatus are provided. The tensioning apparatus applies a tensile force through the load sensing device and the selected test specimen. When a selected specimen is so coupled, the load sensing device outputs a signal representative of the tensile force applied to the selected specimen.

In a presently preferred embodiment the static load tester further comprises sensory detection means coupled to the load sensing device for receiving the signal representative of a tensile load and converting the signal into a sensory output sensorily detectable by a person. Preferably the sensory detection means includes a digital read-out display for displaying the magnitude of the tensile force applied to the load sensing device and any of the selected test specimens coupled to the load sensing device.

Because of the I-beam, the static load tester has dual channel testing capacity. Included is a second load sensing device disposed within the second channel of the I-beam. A first end of the sensor is coupled to the I-beam. The sensor has a second end, as well.

There are second tensioning apparatus coupled to the I-beam, within the second channel, and opposite the second load sensing device. Included also are second means for coupling a second selected test specimen between the second end of the second load sensing device and the second tensioning apparatus. These function as disclosed above with respect to the first load sensing device, the first coupling means and the first tensioning apparatus.

With dual channel testing capacity switched selection means having a first input coupled to the first load sensing device's output signal, a second input coupled to the second load sensing device's output signal, selection means for selecting which of the first and the second input signals will be output from the switched selection means, and an output coupled to the digital read-out display.

Ideally, a test facility will include a plurality of the static load testers, each having the dual channel capacity. Each will also have its first and second load sensing devices, constituting a plurality of the first and second load sensing devices. Each of the plurality of first and second load sensing devices outputs a signal representative of tensile load, constituting a plurality of the signals, each representative of a tensile load.

Included are switch selection means having a plurality of inputs each accepting a selected one of the plurality of the signals representative of a tensile load. The selection means has an output means for outputting a selected one of the plurality of the signals. There is a digital display means having an input coupled to the output means for selecting one of the plurality of signals output by the switch selection means and displaying the selected signal as a digital readout representative of a tensile load.

Conveniently, the first means for coupling a selected test specimen further includes means for coupling a plurality of the selected test specimens in tandem between the second end of the load sensing device and the tensioning apparatus.

DETAILS OF BEST MODE FOR CARRYING OUT THE INVENTION

Figure 1:
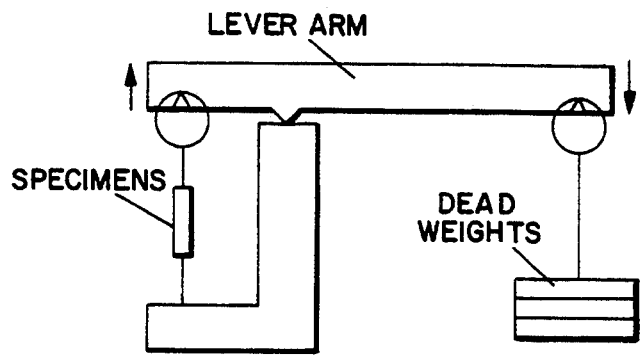
FIG. 1 shows a typical prior art testing device.

For purposes of promoting an understanding of the principles of the invention, reference will now be made to the embodiments illustrated in the drawings and specific language will be used to describe the same. It will nevertheless be understood that no limitation of the scope of the invention is thereby intended. Alterations and modifications of the illustrated device are contemplated, as are such further applications of the principles of the invention as would normally occur to one skilled in the art to which the invention pertains.

As noted in the prior art discussion, FIG. 1 shows a conventional lever arm tester.

Figure 2:
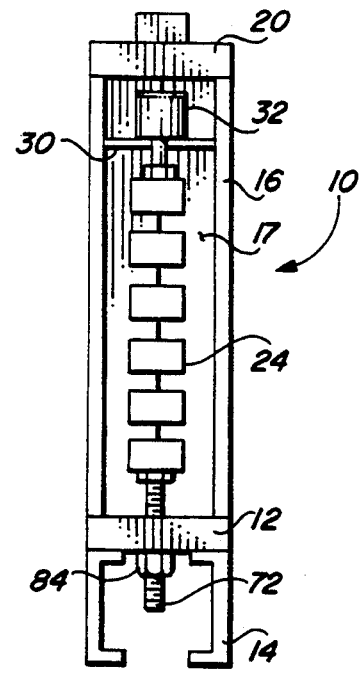
FIG. 2 shows a front elevational view of a static load tester of the present invention.
Figure 5:
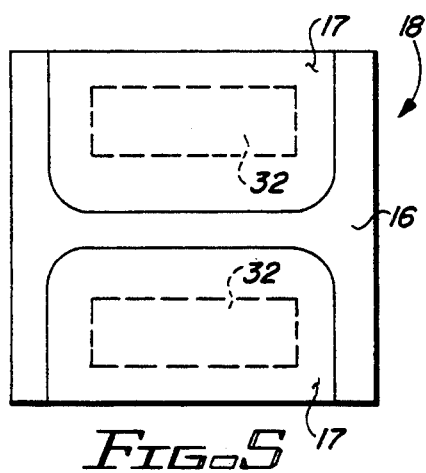
FIG. 5 shows a top view of a multiple testing unit, further showing placement of load cells within an I-beam frame.
Figure 7:
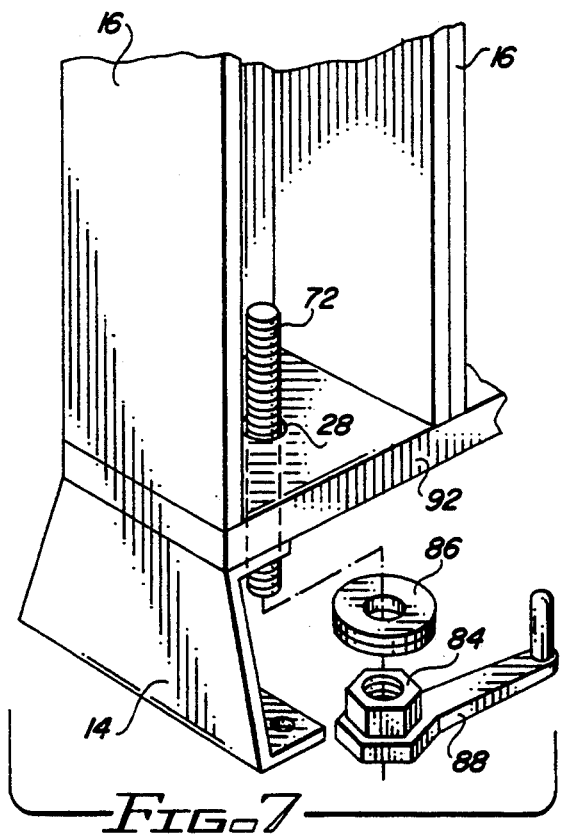
FIG. 7 shows an exploded view of the lower portion of a static load tester, further showing components of the load application system.

The discussion of the instant invention begins with FIG. 2. Static load tester 10 is comprised of bottom plate 12 which rests on fixed support legs 14. Fixed support legs 14 may be fixed to a floor or bench top for stability. I-beam frame 16 is fixed at one of its ends to bottom plate 12 such that its longitudinal axis is perpendicular to the plane of bottom plate 12. Use of I-beam frame 16 allows for economy of design and compactness in that static load tester 10 can be incorporated into each of front and back channels 17 of I-beam frame 16, thereby providing double testing unit 18 as shown in FIG. 5.

Top plate 20 is fixed to an upper end of I-beam frame 16. I-beam frame 16 is of sufficient length so as to accommodate the interconnecting hardware of static load tester 10 hereinafter referred to as functional components 22 and at least eight test specimens 24 when fixed end to end in static load tester 10. Functional components 22 are detailed in FIG. 8 and discussed later. The size and strength of I-beam frame 16, top plate 20, and bottom plate 12 are sufficient to accommodate the size of functional components 22 of static load tester 10 when used in conjunction with at least eight test specimens 24, and to accommodate the tensile forces applied during testing so as to minimize variation and inaccuracy which might otherwise result from distortion.

Figure 4:
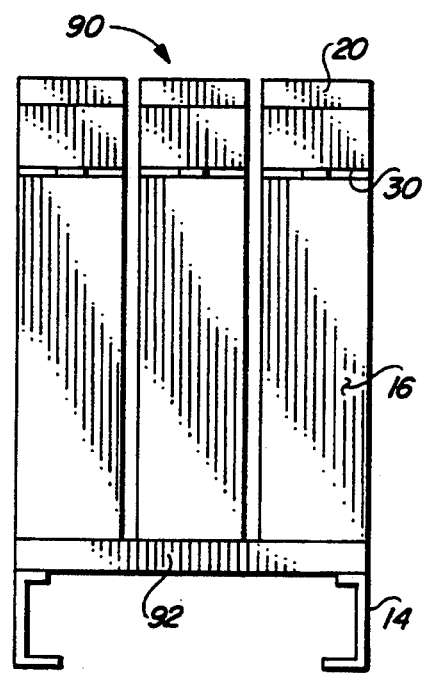
FIG. 4 shows a front elevational view of a multiple testing unit frame.

Functional components 22 of load tester 10 are centrally located within an open channel 17 of I-Beam frame 16, and are aligned parallel to its longitudinal axis. Top plate hole 26 and bottom plate hole 28 are both centrally located with respect to the corresponding open channel 17 of I-beam frame 16. Electronic load cell protective shield 30 is fixed within the open channel 17 and near the upper end of I-beam frame 16 substantially as shown in FIGS. 4 and 6.

Figure 6:
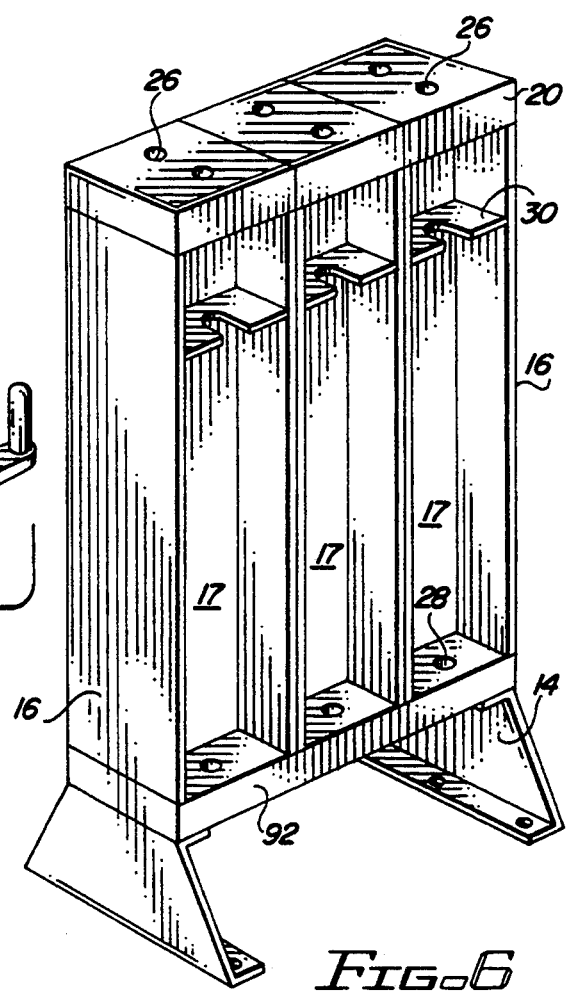
FIG. 6 shows an elevational perspective view of a multiple testing unit frame.
Figure 8:
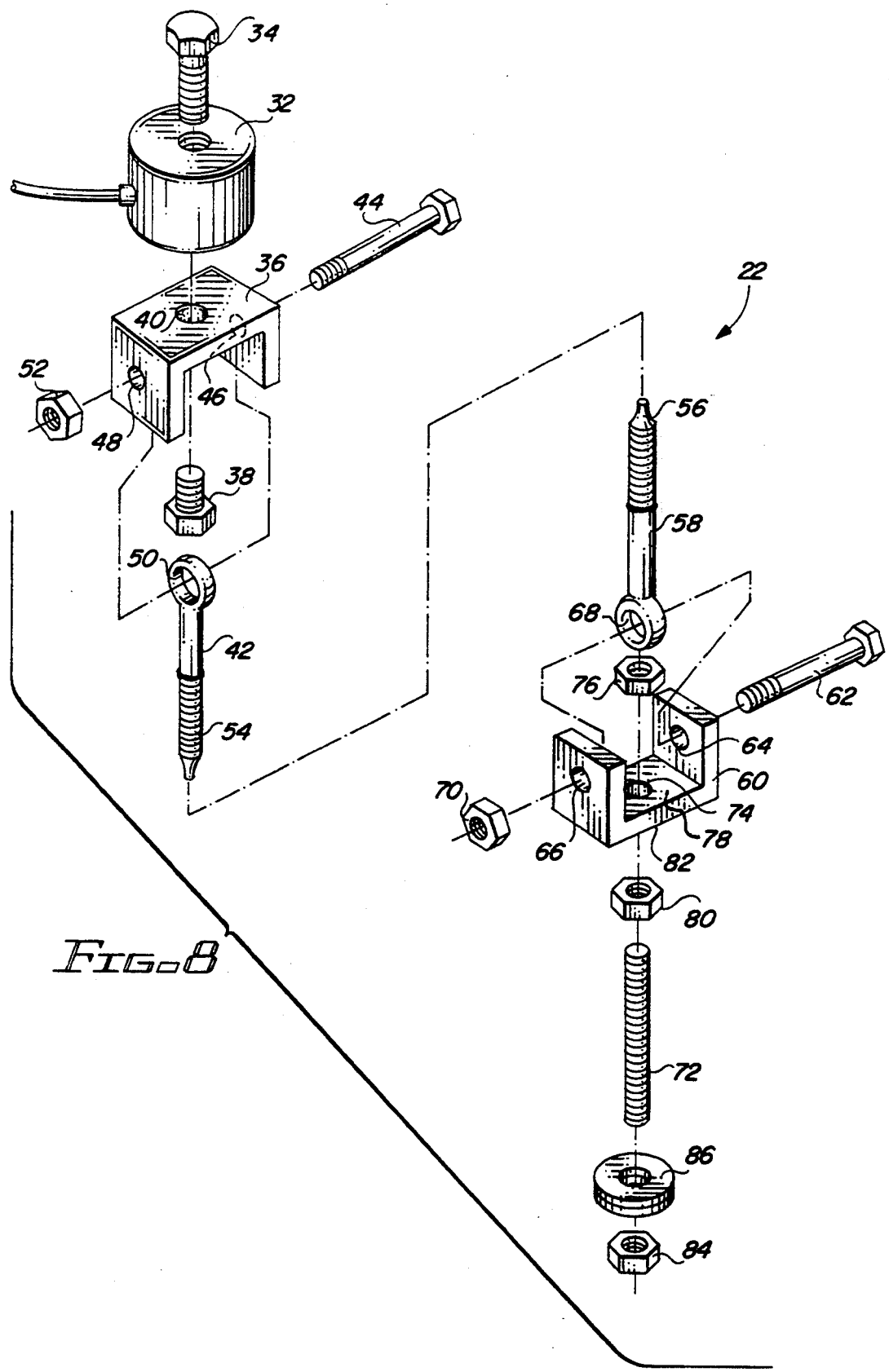
FIG. 8 shows component parts of the test specimen holding and loading system, absent the frame.

Referring to FIGS. 2, 6, and 8, electronic load cell is held in position between protective shield 30 and top plate 20 with bolt 34 which passes through top plate hole 26 to engage electronic load cell 32. Upper clevis 36 is connected to electronic load cell 32 with bolt 38 which passes through upper clevis top hole 40 to engage electronic load cell 32. Upper rod end bearing 42 is rotationally connected to upper clevis 36 with bolt 44 which passes through upper clevis side holes 46 and 48, and upper rod end bearing hole 50. Bolt 44 is secured with threaded nut 52. Upper rod end bearing 42 is adjustably connected to upper specimen holder 54.

Lower specimen holder 56 is adjustably connected to lower rod end bearing 58, which is rotationally connected to lower clevis 60 with bolt 62 which passes through lower clevis side holes 64 and 66, and lower rod end bearing hole 68. Bolt 62 is secured with threaded nut 70. Threaded rod 72 passes through lower clevis bottom hole 74 and is engaged with threaded nut 76 which comes into contact with inner surface 78 of lower clevis 60. Threaded rod 72 is held in a fixed position relative to lower clevis 60 through engagement with threaded nut 80 which comes into contact with outer surface 82 of lower clevis 60.

The lower end of threaded rod 72 passes through bottom plate hole 28 and is engaged with threaded nut 84. Thrust bearing 86 is placed between threaded nut 84 and the lower end of threaded rod 72. Crank handle 88 is used to rotate threaded nut 84 which causes threaded rod 72 to move in a downward direction relative to bottom plate 12. This results in application of a selected level of tension on test specimens 24 mounted between upper specimen holder 54 and lower specimen holder 56.

Figure 3:
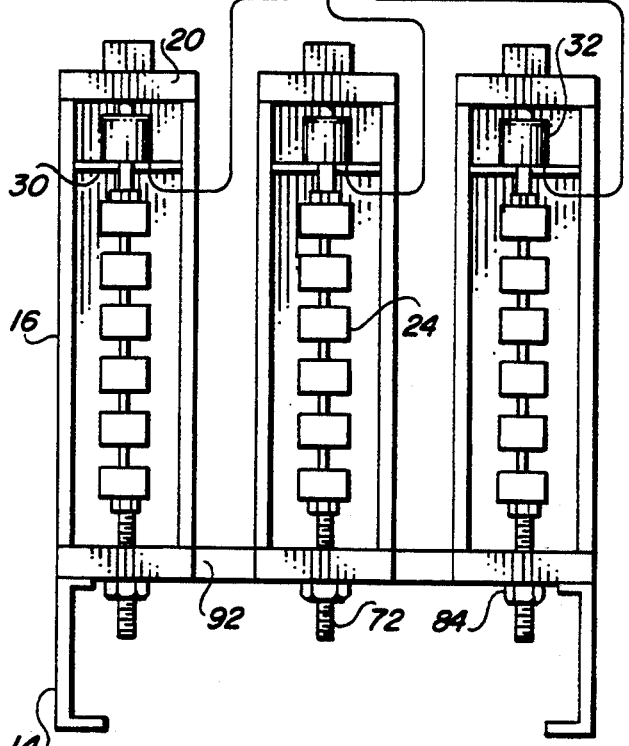
FIG. 3 shows a front elevational view of a multiple testing unit of the present invention with electronic switch box and readout.

The best mode of the present invention further comprises multiple testing unit 90, incorporating multiple static load testers 10 as shown in FIGS. 3, 4, and 6. Each I-beam frame 16 has the capacity to provide a double testing unit 18 as shown in FIG. 5. Additionally, when multiple double testing units 18 are fixed side by side on common bottom plate 92 as shown in FIG. 6, a plurality of static load testers 10 can be incorporated into a multiple testing unit 90. The number of static load testers 10 in each multiple testing unit 90 is double the number of I-beam frames 16 incorporated into unit 90. Although multiple testing unit 90 has a common bottom plate 92, each incorporated I-beam frame 16 must have its own top plate 20 to minimize the variational effects of loading at one static load tester 10 on other static load testers 10 within multiple testing unit 90.

Multiple testing unit 90 is equipped with electronic readout 94 (FIG. 3) which displays the level of tensile force exerted on test specimens 24 during testing. Coupling each static load tester's electronic load cell 32 to switch box 96, which is in turn coupled to electronic readout 94, provides the user with a tensile force reading from any desired individual static load tester 10 in multiple testing unit 90 simply by dialing switch box 96 to the desired tester 10. Thus, one electronic readout 94 accommodates multiple testing unit 90.

Those skilled in the art will conceive of other embodiments of the invention which may be drawn from the disclosure herein. To the extent that such other embodiments are so drawn, it is intended that they shall fall within the ambit of protection provided by the claims herein.

Having described the invention in the foregoing description and drawings in such clear and concise manner that those skilled in the art may readily understand and practice the invention.

That which is claimed is:

1. A static load tester, to replace prior art, lever arm testers, for applying a tensile load to selected specimens over an extended period of time, said load tester comprising:

an I-beam support column having first and second channels;

a first load sensing device for outputting a signal representative of a tensile load applied to said device, said device being disposed within said first channel of said I-beam and having a first end coupled to said I-beam;

said load sensing device having a second end;

first tensioning apparatus coupled to said I-beam, within said first channel and disposed opposite said load sensing device; and first means for coupling a selected test specimen between said second end of said first load sensing device and said first tensioning apparatus, said first tensioning apparatus applying a tensile force through said first load sensing device and a said selected test specimen, when said selected specimen is so coupled, said first load sensing device outputting a signal representative of the tensile force applied to said selected specimen so coupled.

2. The static load tester of claim 1 further comprising sensory detection means coupled to said load sensing device for receiving said signal representative of a tensile load and converting said signal into a sensory output sensorily detectable by a person.

3. The static load tester of claim 2 wherein said sensory detection means includes a digital read-out display for displaying the magnitude of the tensile force applied to said load sensing device and any said selected test specimens coupled to load sensing device.

4. The static load tester of claim 1 having dual channel testing capacity, and comprising:

a second load sensing device disposed within said second channel of said I-beam, having a first end coupled to said I-beam, and having a second end;

second tensioning apparatus coupled to said I-beam, within said second channel, opposite said second load sensing device; and second means for coupling a second selected test specimen between said second end of said second load sensing device and said second tensioning apparatus, functioning as disclosed in claim 1 with respect to said first load sensing device, said first coupling means and said first tensioning apparatus.

5. The static load tester of claim 4 further comprising sensory detection means coupled to said second load sensing device for receiving said signal representative of a tensile load and converting said signal into a sensory output sensorily detectable by a person.

6. The static load tester of claim 5 wherein said sensory detection means includes a digital read-out display for displaying the magnitude of the tensile force applied to said load sensing device and any said selected test specimens coupled to load sensing device.

7. The static load tester of claim 6 further comprising switched selection means having a first input coupled to said first load sensing device's output signal, a second input coupled to said second load sensing device's output signal, selection means for selecting which of said first and said second input signals will be output from said switched selection means, and an output coupled to said digital read-out display.

8. A plurality of said static load testers of claim 4, each having said dual channel capacity:

each having said first and second load sensing devices constituting a plurality of said first and second load sensing devices;

each of said plurality of first and second load sensing devices outputting a signal representative of tensile load, constituting a plurality of said signals, each representative of a tensile load;

switch selection means having a plurality of inputs each accepting a selected one of said plurality of said signals representative of a tensile load, and output means for outputting a selected one of said plurality of said signals; and digital display means having an input coupled to said output means for selecting one of said plurality of signals output by said switch selection means and displaying said selected signal as a digital readout representative of a tensile load.

9. The static load tester of claim 8 wherein said first and said second means for coupling selected test specimens further include means for coupling a plurality of said selected specimens in tandem for simultaneous tensile testing.

10. The static load tester of claim 4 wherein said first and said second means for coupling selected test specimens further include means for coupling a plurality of said selected specimens in tandem for simultaneous tensile testing.

11. The static load tester of claim 1 wherein said first means for coupling a selected test specimen further includes means for coupling a plurality of said selected test specimens in tandem between said second end of said first load sensing device and said first tensioning apparatus.

* * * * *